US007888037B2

(12) United States Patent
Bisen et al.

(10) Patent No.: US 7,888,037 B2
(45) Date of Patent: Feb. 15, 2011

(54) DIAGNOSTIC KIT FOR DETECTING PULMONARY AND EXTRA PULMONARY TUBERCULOSIS

(75) Inventors: Prakash Singh Bisen, New Delhi (IN); Ram Pramod Tiwari, Gwalior (IN)

(73) Assignees: Department of Biotechnology, New Delhi (IN); Madhav Institute of Technology and Science, Gwalior (IN)

( * ) Notice: Subject to any disclaimer, the term of this patent is extended or adjusted under 35 U.S.C. 154(b) by 200 days.

(21) Appl. No.: 10/590,118

(22) PCT Filed: Feb. 21, 2005

(86) PCT No.: PCT/IN2005/000063

§ 371 (c)(1),
(2), (4) Date: Jun. 11, 2007

(87) PCT Pub. No.: WO2005/080987

PCT Pub. Date: Sep. 1, 2005

(65) Prior Publication Data

US 2007/0287165 A1  Dec. 13, 2007

(30) Foreign Application Priority Data

Feb. 19, 2004 (IN) .......................... 226/DEL/2004

(51) Int. Cl.
*G01N 33/53* (2006.01)
*A61K 39/04* (2006.01)

(52) U.S. Cl. ...................... 435/7.1; 435/7.2; 435/253.1; 424/9.1; 424/9.2; 424/130.1; 424/164.1; 424/184.1; 424/234.1; 424/248.1

(58) Field of Classification Search .................. 424/9.1, 424/9.2, 130.1, 164.1, 184.1, 234.1, 248.1; 435/7.1, 7.2, 253.1
See application file for complete search history.

(56) References Cited

PUBLICATIONS

Bisen, Prakash, et al., "Analysis of the Shotgun Expression Library of the *Mycobacterium tuberculosis* Genome for Immunodominant Polypeptides: Potential Use in Serodiagnosis", Clinical and Diagnostic Laboratory Immunology, (Nov. 2003), vol. 10, No. 6, pp. 1051-1058, American Society for Microbiology.

Garg, Sanjay K., et al., "Diagnosis of Tuberculosis: Available Technologies, Limitations, and Possibilities", Journal of Clinical Laboratory Analysis, (2003), vol. 17, pp. 155-163, Wiley-Liss, Inc.

*Primary Examiner*—Rodney P. Swartz
(74) *Attorney, Agent, or Firm*—The Webb Law Firm

(57) ABSTRACT

A diagnostic kit for detecting pulmonary and extra pulmonary tuberculosis comprising a test card "TB Screen" coated with a hydrophobic material, antigen suspension, positive and negative control.

15 Claims, No Drawings

DIAGNOSTIC KIT FOR DETECTING PULMONARY AND EXTRA PULMONARY TUBERCULOSIS

FIELD OF THE INVENTION

This invention relates to a diagnostic kit for detecting pulmonary & extra pulmonary tuberculosis.

BACKGROUND OF THE INVENTION

The conventional methods for detecting tuberculosis is time consuming & labour-intensive. Acid-fast bacilli (AFB) staining is considered to be insensitive (requiring 10,000 organism/ml of sputum for smear positive result with 100× microscope, refer Todar's Text Book of Bacteriology Online). ELISA-KP 90 is also known to be of low sensitivity and specificity (cut-off value>1.0 +ve, and <0.8 –ve test result) and requires sophisticated infrastructure as also the hypersensitivity based Tuberculin Skin Test (Montaux test), which lacks sensitivity, and specificity in BCG vaccinated patient. In the same way MYCODOT is inconvenient for HIV correlated individuals (14). Bactec-460 radiometric system (Becton Dickinson Instrument Systems, Sparks, Md. USA) is sensitive and is being used globally, but it took 5-10 days time for interpretation of the results and need for safe disposal of the radioactive waste products whereas the Roche molecular system PCR based product) are though sensitive requires very costly infrastructure and technical expertise (2 and 4).

OBJECTS OF THE INVENTION

An object of this invention is to propose a diagnostic kit for detecting tuberculosis.

A further object of this invention is to propose a diagnostic kit which is economical and easy to handle.

A still further object of this invention is to propose a diagnostic kit based on liposome agglutination.

Another object of this invention is to propose a diagnostic kit which is sensitive and specific as it is based on a specific antigenic, antibody reaction.

Still another object of this invention is to propose a diagnostic kit which helps in fast detection of tuberculosis.

BRIEF DESCRIPTION OF THE INVENTION

According to this invention there is provided a diagnostic kit for detecting pulmonary & extra pulmonary tuberculosis comprising a test card "TB Screen" coated with a hydrophobic material, antigen suspension, positive and negative control.

In accordance with this invention there is provided a method of detecting tuberculosis using the kit comprising applying positive control, negative control & test sample each in circular motion on the test card zone (FIG. 3) coated with hydrophobic material adding said antigen suspension of lipsome (FIG. 4) in the presence of Sandun black 8 dye as an indicator and/or a marker to each of the positive, negative & test sample to interpret the results, clumping of specific antigen and anti body as dark blue agglutination was observed in positive control and the test sample which contain the active tuberculosis infection.

DETAILED DESCRIPTION OF THE INVENTION

The *Mycobacterium tuberculosis* $H_{37}Rv$ (ATCC-27294) strains was grown on Sautons media till late log phase (2-3 month) and/or Middle Brook 7H9 or 7H12B both supplemented with 10% albumin dextrose and catalyst (ADC) at 37° C. (2-3 weeks). The cells were harvested by centrifugation (5000-10,000 g for 10-20 min) at 4°-40° C., the pellet was washed with (phosphatic buffet saline (PBS: 100 mM, pH 7.2-7.6), resuspended with TEN buffer, pH 8.0-8.5 (10 mM Trs HCl, 1 mM EDTA, 100 mM NaCl) and heat inactivated at 70°-80° C. (water bath) for 30-45 min. followed by sonication (15% pulse 150 W) and lyphilized. The glycolipid antigens were extracted according to the procedure mentioned in the literature (12 and 13) with the slightly modification in the procedure. In brief, the sonicated and lyophilized powder of mycobacterial cells (10-15 g was taken into a glass reagent bottle and to it 100-150 ml of chloroform and methanol mixture (2:1) was added. This was stirred at room temperature for 50-60 minutes and filtered through Whatman filter paper No 1. A ⅕ volume of 0.7% KCl (20.0 ml) was added to the filtrate and was uniformly shaken for 5-6 times. The suspension was transferred to a separating funnel and kept at 2-8° C. for overnight until two distinct layers were separated. The lower organic phase was washed with ⅙ volume of washing solvent (Chloroform, methanol, and water at a ratio of 3:48:47 respectively) in similar manner by keeping at 2-8° C. for overnight. The upper aqueous phase was removed and lower organic phase was retained after filtering. The organic phase was dried by evaporating the solvent in rotatory solvent evaporator at 40-50° C. The moisture was removed by flushing the dried mixture with nitrogen gas. Neutral lipids were removed from the dried mixture by adding 300-600 ml of chilled acetone vortexing it for 10-20 minutes and filtering it through Whatman No. 1. This step was repeated until the lipids in the flask became whitish or colorless. This was filtered through Whatman No. 1 and the filtrate was discarded. The lipids present on the filter paper were dissolved with chloroform:methanol (2:1) and transferred to the round bottom (RB) flask. The solvent was rotary evaporated under reduced pressure at 40-50° C. The crude preparation was reconstituted in 10-16 ml of C:M (2:1) and stored at –20° C. for further use.

Purification of Antigen(s):

The silica gel H(S.D. Fine Chemical, India) was activated at 100-110° C. for 1-1.30 hours (hot air oven) was packed with, glass column (2.6.times.30 cm) with manual tapping in which one end was plugged with a cork and a known quantity of crude material (1.0 g/5 ml, stock) was loaded on another side. The column was run in an ascending direction in a on chromatographic jar (4.5.times.25 cm) with 150-200 ml of purification solvent, (mobile phase) in a ratio of 66:25:4 chloroform:methanol:water at room temperature following the procedure in reference 7.

The column was removed from the chromatographic jar and placed on fume hood to evaporate the solvent from the column. A 10 cm length of each fraction was carefully scrapped using clean glass rod to separate the individual molecules that were adsorbed with the silica gel depending upon the mobility and Retardation Factor (RF) value (46.6, 63.4, 68.3, 67.2 and 72.4%) of the individual molecules. The individual fractions were collected and placed into clean dry glass test tubes, which were labeled with respective fraction number, Ten ml of extraction solvent (mixture of chloroform: methanol 2:1) was added to each test tubes and kept at room temperature for 30-40 minutes. The purity of eluted material was analyzed by TLC and the selected fraction were further filtered through Whatman filter paper No. 1 to remove the silica gel from the samples. The pure fractions were pooled and these were characterized by Eastern blot hybridization (FIG. 1) and ELISA followed by biochemical and immunological characterization of glycolipid antigens fractions.

Method for the Construction of Liposomal Antigens:

Liposome was prepared (FIG. 4) as described previously with some modification. In brief Phophotidylcholine 100-150 mg; cholesterol, 450-500 mg (Sigma, USA); antigenic suspension (Cocktail) 16-25 mg; and dye 50-100 μl (1.0-2.0%. Sudan black B in chloroform) were taken uniformly in a round bottom flask while addition of 10-25 ml of absolute alcohol (99.9%) Hyman, Germany). Solvent was evaporated by rotatory vacuum evaporator under reduced pressure, and the dried mixture was further dissolved in 40-50 ml of absolute alcohol (99.9% Hyman, Germany) and were kept at 4° 10° C. for 1-1.30 hrs. Sucrose solution (4-8 ml; 150 Mm) was taken in a polypropylene centrifuge tube (capacity 35 mil) and to that 4-5 ml of the above alcoholic antigen suspension was gently added while vortexing. The centrifuge tubes containing the above suspension were kept over night at 4° 10° C. for liposome swelling, vortexed with 10-15 ml of PBS (pH 6.5) buffer and centrifuged at 10,000 g for 10-20 min (Beckman, USA). The supernatant was discarded and the pellet was resuspended with 25-50 ml of RP buffer, pH 7.2 ($NaH_2PO_4.2H_2O$, 10 mM; $KH_2PO_4$, 10 mM; EDTA, 10 mM; choline chloride, 10% and thiomersal, 0.1%). This was stored at 4° 10° C. for further use and utilized as liposomal antigen reagent for the kit.

Preparation of Phosphatidylcholine:

Phosphatidylcholine (PC) was prepared in house to reduce the cost of the test. Those skilled in the art are aware of purification of PC from egg yolk. In brief, 24 eggs ere taken and albumin portions were removed. The collected yolk was extracted with 750 ml of chloroform:methanol (2:1) by stirring for 30 minutes and filtered through Whatman No. 1. The filterate was deproteinized with one fifth volume of 0.7% of KCl. To the organic layer so obtained, washing was performed with 3:48:47 of chloroform:methanol:water. Moisture was removed by using benzene. Solvent was evaporated with the aid of rotary vacuum and a dried film of lipid was obtained. Neutral lipids were removed as described above with chilled acetone. Empty weight of round bottom flask was taken. The flask was weighed along with the dried lipid film. 37.5 g of crude lipid was isolated. The crude product was further purified by silica gel H chromatography and purified PC was characterized by thin layer chromatography (19).

Preparation of Positive Control for Test:

The mixture of purified glycolipid antigens (1-2 mg) in PBS (pH7.2) were emulsified with an equal volume (1.0-2.0 ml) of Freunds Incomplete Adjuvant (IFA) and immunized to (2-8 months old) young rabbit subcutaneously (100-500 μl/rabbit) and boosted in similar manner after 15 days interval thrice and titer was monitored (1:60-1:120) periodically. A number of rabbits were inoculated in the same manner.

Rabbits were bled one month after the third booster and serum was obtained. The reactivity of serum was checked with the liposome antigen suspension as described in the test procedure given in next paragraph and the reactivity titer was checked. A booster administration of the antigen (50-100-500 μl) was again repeated. An enhanced titer of about 1:64 to 1:128 was obtained after seven days to fifteen days of booster dosage. Best reactivity titer was obtained. The serum was diluted to optimum reactivity titer in 1×PBS and 0.1% sodium azide was added as a preservative, and the stock was frozen until further use.

The 4-6 month old rabbits were immunized with the above antigens and bled periodically. The serum was oslated and used as a positive control for the kits, where as normal young rabbits were used for negative control.

Method of Testing:

All the components of the (TB Screen test) kit, such as positive control, negative control, liposomal antigen suspension (FIG. 2) and sample to be tested were brought to room temperature before performing the testing. The positive control, negative control and freshly procured or frozen test serum sample (25 μl) were added and spaced evenly inside the circular zone of hydrophobic material coated plastic slide (FIG. 3). Thereafter, 25 μl of liposome antigen was added to each zone and the card was gently swirled for 4 minutes.

Freshly procured or frozen test serum samples (25 μl) were spread evenly inside the circular zone of hydrophobic material coated plastic slide. For convenience, zones 1 and 2 were spread with the positive (anti-rabbit serum) and negative control (normal rabbit serum) respectively, to interpret the results. The liposome antigenic suspension (25 μl) as prepared previously was added to each circular zone including zones 1 and 2 and the card was gently swirled for 4 minutes. The clumping of specific antigen and antibody as dark blue agglutination were observed in positive control as well as in those samples which contain antibodies against mycobacterial glycolipid with active tuberculosis (FIG. 3A) infection and considered to be positive, where as absence of clumping on the test card were considered as negative result. The peripheral drying on the circular zone indicated indeterminate results (FIG. 3B1), which require further confirmation within 15-30 days, as these samples contained undetectable levels of antigen concentration in the specimens.

Example 1

Sera

Sera collected from outdoor patient departments (OPD) from different hospitals and pathology centers in India were enrolled in the present study to cover maximum population diversity. The patients were diagnosed with TB on the basis of clinical and radiological evaluation as well as smear staining and sputum culture of samples. Sera samples from both categories, which include pulmonary and extra-pulmonary tuberculosis sera were included in the study. A total of three hundred and twenty four (324) tuberculosis sera were studied.

Sera from healthy individuals without any clinical symptoms of TB were included as negative controls to evaluate specificity criterion of the test. Most of these were obtained form BCG vaccinated subjects. The non-TB sera generally belonged either to health individuals or to patients suffering from a variety of diseases other than tuberculosis. The sera that were stored frozen and were used within one year. Also five hundred and eleven (511) tuberculosis negative sera were included in this testing. The details of criteria used in selection of sera is a follows:

| | |
|---|---|
| Smear Negative, Culture Positive pulmonary cases | 52 |
| Smear Positive, Culture Positive, pulmonary cases | 180 |
| Extra-pulmonary, Culture Positive cases | 35 |
| Relapse pulmonary cases | 57 |
| Drug treated, clinically negative cases | 60 |
| Healthy household contacts | 50 |
| BCG vaccinated children | 15 |
| Hepatitis B positive samples | 15 |
| Sera from common infections other than TB | 27 |
| Normal human sera | 344 |

Example 2

An overall sensitivity of 98.68% was obtained using a panoply of three hundred and twenty four tuberculosis sera, out of which 20 sera showed indeterminate results that were not included in the sensitivity and specificity calculations, as per method adopted by WHO. An overall specificity of 98.78% was obtained using five hundred and eleven non-tuberculosis sera.

Sera from 15 children who were recently immunized with BCG were tested for any cross-reactivity of the test with vaccination. None of the sera yielded positive results, thereby indicating the suitability of the test in BCG vaccinated populations.

Fifteen cases of Hepatitis B positive samples were evaluated for cross reactivity. There was no reaction in any of the sera tested. Four Hepatitis B sera were tested with the kit at Hopkins Research Institute, Mumbai with nil reactivity (not included in inhouse study table).

Out of 27 sera from other common infections, 25 showed clear negative and only two showed indeterminate results. These subjects were needed to be evaluated after 15-20 days to understand the progress of tuberculosis, but unfortunately, it could not be done. Indeterminate results were omitted from specificity and sensitivity calculations.

Results of inhouse studies are tabulated as follows:

TABLE 1

STUDIES PERFORMED ON TUBERCULOSIS POPULATION

| SERA DETAILS | RESULTS |
|---|---|
| Number of tuberculosis sera tested = 324 | positive = 300<br>negative = 4<br>indeterminate = 20**<br>SENSITIVITY = 98.68% |
| Smear Negative, Culture Positive pulmonary cases - 52 | positive = 47<br>negative = 2<br>indeterminate = 3 |
| Smear Positive, Culture Positive, pulmonary cases - 180 | positive = 175<br>negative = —<br>indeterminate = 5 |
| Extrapulmonary cases, Culture Positive - 35 | posltive = 28<br>negative = 2<br>indeterminate = 5 |
| Relapse pulmonary cases - 57 | positive = 50<br>negative = —<br>indeterminate = 7 |

**indiscriminate samples were not included in sensitivity & specificity calculations as per WHO methodology.

TABLE 2

STUDIES PERFORMED ON NON-TUBERCULOUS SERA

| | |
|---|---|
| Number of non-TB sera tested = 511 | positive = 488<br>negative = 6<br>indeterminate = 17**<br>SPECIFICITY = 98.78% |
| 5. Drug treated, clinically negative cases - 60 | positive = —<br>negative = 51<br>indeterminate = 9 |
| 6. Healthy household contacts - 50 | positive = —<br>negative = 50<br>indeterminate = — |
| 7. BCG vaccinated children - 15 | positive = —<br>negative = 15<br>indeterminate = — |
| 8. Hepatitis B positive samples - 15 | positive = —<br>negative = 15—<br>indeterminate = |

TABLE 2-continued

STUDIES PERFORMED ON NON-TUBERCULOUS SERA

| | |
|---|---|
| 9. Sera from common infections (Not TB) - 27 | positive = —<br>negative = 25<br>indeterminate = 2 |
| 10. Normal human sera - 344 | positive = 6<br>negative = 332<br>indeterminate = 6 |

**indiscriminate samples were not included in sensitivity & specificity calculations as per WHO methodology.

Excellent results were obtained when using fresh sera from subjects under investigation of test results. Frozen sera can be tested after thawing, but repeated freeze thawing (more than 4-5 times) of samples might affect the outcome.

REFERENCES

1. Bangham, A. D., Standish M. M, Watkins JC Diffusion of Univalent Ions Across the Lameliae of Swollen Phospholipids, J. Mol. Biol., (1965), Vol. 13, pp. 238-252.
2. Bisen, P. S., Garg, S. K., Tiwan R. P., Tagore, P. R. H., Chandra, R., Karnik, R. Thaker, N., Desai, N., Ghosh, P. K., Fraziano, M., Colizzi, V.; "Analysis of Shotgun Expression Library of *Mycobacterium Tuberculosis* Genome for Immunodominant Polypeptide: Potential Use in Serodiagnosis", Clin and Diagn. Lab Immunol., (2003), Vol. 6, pp 1051-1058.
3. Charpin, D. H., Gevaudan, H., Saadjian, M. J., De Micco, P., Arnaud, A., Vervloet, D., Charpin, J., "Value of ELISA Using A-60 Antigen in the Diagnosis of Active Pulmonary Tuberculosis", Am. Rev. Respir. Dis., (1990), Vol. 142, pp. 380-388.
4. Garg, S. K., Tiwan, R. P., Tiwan, D. Singh, R., Malhotra, D., Ranmani, V. K., Prasad, G. B. K. S., Chandra, R., Fraziano, M., Colizzi, V., Bisen, P.S., "Diagnosis of Tuberculosis Available Technologies, Limitations and Possibilities", J. Clin. Lab Anal., (2003), Vol. 17, pp. 155-163.
5. Hines, M. E., Jaynes, J. M., Barker, S. A., Newton, J. C., Enright, F. M., Snider, T. G., "Isolation and Partial Characterization of Glycolipid Fractions from *Mycobacterium avium* serovar 2 (*Mycobacterium paratuberculosis* 18) that Inhibit Activated Macrophages Infection and Immunity", (1993) Vol. 61, pp. 1-7.
6. Konstantin, P. K., Claudia, L. M., Roberto, C., Anna, H., Alan, W., Gennaro, M. L., "Use of *M. tuberculosis* Complex-specific Antigen Cocktails for a Skin Test Specific for Tuberculosis Infection and Immunity", (1998), Vol. 66, pp. 3606-3610.
7. Lepage, M., "Isolation and Characterization of an etherified form of Sterile Glucoside", J. Lipid Res., (1964), Vol. 53, pp. 587-592.
8. Papa, F., Cruaud, P., Luquin, M., Torei, M. F., Gohand, K. S., David, H. L., "Isolation and Characterization of Serologically Reactive Lipooligosaccharides from *M. tuberculosis*", Res. Microbiol., (1993), Vol. 144, pp. 91-99.
9. Papa, F. P., Cruaud, P., David, H. L., "Anigenicity and Specificity of Selected Glycolipid Fractions from *M. tuberculosis*", Res. Microbiol., (1989), Vol. 140, pp. 569-578.
10. Payne, S. N., Draper, P., Rees, R. J. W., "Serological Activity of Purified Glycolipid from *Mycobacterium leprae*", Int. J. Lepr., (1982), Vol. 50, pp. 220-221.
11. Ridell, M., Wallestrom, G., Minhikin, D. E., Bolton, R. C., Magnusson, M. A., "Comparative Serological Study of Antigenic Glycolipids from *M. tuberculosis*", Tubercle Lung Dis. (1992), Vol. 73, pp. 101-105.

12. Reggiardo, Z., Middlebrook, G., "Serologically active glycolipid Families from *Mycobacterium Bovis* BCG I. Extraction, purification and immunologic studies", Am. J. Epidemiol., (1974a), Vol., 100, pp. 469-476.
13. Reggiardo, Z., Middlebrook, G., "Serologically active glycolipid Families from *Mycobacterium Bovis* BCG II. Serologic studies on human sera", Am. J. Epidemiol., (1974b), Vol., 100, pp. 477-486.
14. Somi, G. R., Grien, R. J. O., Mfinanga, G. S. Ipuge, Y. A., "Evaluation of the Mycodor™ Test in Patients with Suspected Tuberculosis in a Field Setting in Tanzania", Int. J. Tubercle and Lung Disease, (1999), Vol. 3. pp. 231-238.
15. Work, T. S., Work, E., "Handbook of Laboratory Techniques in. Biochemistry and Molecular Biology", Published by North-Holland Publishing Co., Inc., New York, (1975), Vol. 3.

We claim:

1. A diagnostic kit for detecting pulmonary and extra pulmonary tuberculosis, comprising a test card coated with a hydrophobic material, mixing sticks, a glycolipid from a *Mycobacterium tuberculosis* $H_{37}RV$ antigen suspension intercalated or coupled with a liposome surface, a positive control comprising an antibody that binds to said glycolipid from *Mycobacterium tuberculosis*, and a negative control comprising serum antibodies from a subject not previously exposed to *Mycobacterium tuberculosis*.

2. The kit as claimed in claim 1, wherein said antigen suspension is a liposome antigen and said test card is a plastic slide.

3. The kit as claimed in claim 1, wherein said negative control is prepared from the blood of a normal young rabbit.

4. The kit as claimed in claim 1, wherein said positive control is prepared from a 4 to 6 month old rabbit which is immunized with the glycolipid and bled periodically.

5. A method for testing an individual for tuberculosis comprising the steps of applying a positive control, a negative control and a sample to a hydrophobic material, wherein said positive control is an antibody that binds to a glycolipid from *Mycobacterium tuberculosis*, and wherein said negative control is a serum antibody from a subject not previously exposed to *Mycobacterium tuberculosis*; adding an antigen suspension to said positive, said negative and said sample; and interpreting a result, wherein clumping of a specific antigen in the suspension and an antibody in the positive control and a test sample from the individual is prognostic for an active tuberculosis infection, and wherein the antigen is a glycolipid antigen from *Mycobacterium tuberculosis* $H_{37}Rv$ (ATCC-27294).

6. The method as claimed in claim 5, wherein said antigen suspension is a liposome antigen.

7. The method as claimed in claim 6, wherein said glycolipid antigen is prepared comprising the steps of:
   growing *Mycobacterium tuberculosis* $H_{37}Rv$ (ATCC-27294) strain on Sautons media;
   harvesting cells in the media by centrifugation at 4° to 10° C.;
   subjecting said cells to the step of sonication;
   extracting unpurified antigens from said cells;
   adding chloroform and methanol mixture (2:1) to said unpurified antigens with stirring at room temperature;
   subjecting the mixture to the step of filtration, thereby forming a suspension;
   separating said suspension into an upper aqueous phase and a lower organic phase;
   removing said upper aqueous phase;
   drying said organic phase, thereby forming a solvent containing a lipid; and
   purifying the glycolipid antigen.

8. The method as claimed in claim 5, wherein said antigen suspension is prepared comprising the steps of:
   adding a phosphatidylcholine, a cholesterol, a lipid antigen and a dye in a flask, thereby forming a solvent layer;
   evaporating said solvent layer, thereby forming dried contents;
   dissolving said dried contents in absolute alcohol at 4° to 10° C. for 1 to 2 hours to produce said antigen suspension;
   adding said antigen suspension to a sucrose solution;
   maintaining a temperature of 2° to 8° C. overnight;
   subjecting said suspension to centrifugation, thereby forming a supernatant and a pellet;
   discarding said supernatant; and
   suspending said pellet in a buffer.

9. The method as claimed in claim 6, wherein said glycolipid antigen is further purified using column chromatography.

10. The method as claimed in claim 8, wherein said buffer comprises $NaH_2PO_4 2H_2O$, $KH_2PO_4$, EDTA, Choline Chloride and Thiomersol.

11. The method as claimed in claim 8, wherein said dye is Sudan black B or Sudan red in chloroform.

12. The method as claimed in claim 5, wherein said anti-mycobacterial glycolipid antibody is isolated from a rabbit immunized against the glycolipid antigen from *Mycobacterium tuberculosis* $H_{37}Rv$.

13. The method as claimed in claim 5, wherein said antibodies from a subject not previously exposed to *Mycobacterium tuberculosis* are isolated from a rabbit that has not been exposed to *Mycobacterium tuberculosis*.

14. The method as claimed in claim 5, wherein said anti-mycobacterial glycolipid antibody is coupled onto a surface of a liposome.

15. The method as claimed in claim 13, wherein said rabbit was immunized against a heat inactivated sonicated *Mycobacterium tuberculosis* $H_{37}Rv$ strain.

* * * * *

UNITED STATES PATENT AND TRADEMARK OFFICE
CERTIFICATE OF CORRECTION

| | | |
|---|---|---|
| PATENT NO. | : 7,888,037 B2 | Page 1 of 1 |
| APPLICATION NO. | : 10/590118 | |
| DATED | : February 15, 2011 | |
| INVENTOR(S) | : Bisen et al. | |

It is certified that error appears in the above-identified patent and that said Letters Patent is hereby corrected as shown below:

Column 3, lines 59-60, "antigen (50-100-500 µl)" should read -- antigen (100-500 µl) --

Signed and Sealed this
Tenth Day of May, 2011

David J. Kappos
*Director of the United States Patent and Trademark Office*